(12) United States Patent
Schmidt et al.

(10) Patent No.: US 7,995,570 B2
(45) Date of Patent: Aug. 9, 2011

(54) DEVICE FOR COMMUNICATION

(75) Inventors: Sebastian Schmidt, Weisendorf (DE); Sabine Schaeffer-Kundler, Herzogenaurach (DE)

(73) Assignee: Siemens Aktiengesellschaft, Munich (DE)

( * ) Notice: Subject to any disclaimer, the term of this patent is extended or adjusted under 35 U.S.C. 154(b) by 643 days.

(21) Appl. No.: 12/046,819

(22) Filed: Mar. 12, 2008

(65) Prior Publication Data

US 2008/0228042 A1  Sep. 18, 2008

(30) Foreign Application Priority Data

Mar. 12, 2007  (DE) .................... 10 2007 011 844

(51) Int. Cl.
*H04L 12/50* (2006.01)
*H04L 12/28* (2006.01)
*A61B 5/00* (2006.01)

(52) U.S. Cl. .............. 370/386; 370/422; 600/300

(58) Field of Classification Search .............. None
See application file for complete search history.

(56) References Cited

U.S. PATENT DOCUMENTS

| 6,192,050 B1 * | 2/2001 | Stovall .......................... 370/389 |
| 2002/0062068 A1 | 5/2002 | Gritzbach et al. |
| 2002/0091765 A1 * | 7/2002 | Bocionek ...................... 709/203 |
| 2005/0078082 A1 | 4/2005 | Muralidharan et al. |

FOREIGN PATENT DOCUMENTS

DE  10 2006 033 064 A1  2/2007

* cited by examiner

*Primary Examiner* — Gregory B Sefcheck
*Assistant Examiner* — Srinivasa R Reddivalam
(74) *Attorney, Agent, or Firm* — Schiff Hardin LLP

(57) ABSTRACT

In a device, a method and a system for communication between a control module that can be associated with a local console of a medical modality, an examination module that can be associated with the medical modality, and an administration module that can be associated with an administration entity remote from the medical modality, respective communication units that can be connected among one another are associated with each of the modules and the signals transferred from a respective communication unit are transferred to the communication unit of at least one other module; and the communication unit of the administration module of the remote administration entity can access data of the medical modality.

8 Claims, 1 Drawing Sheet

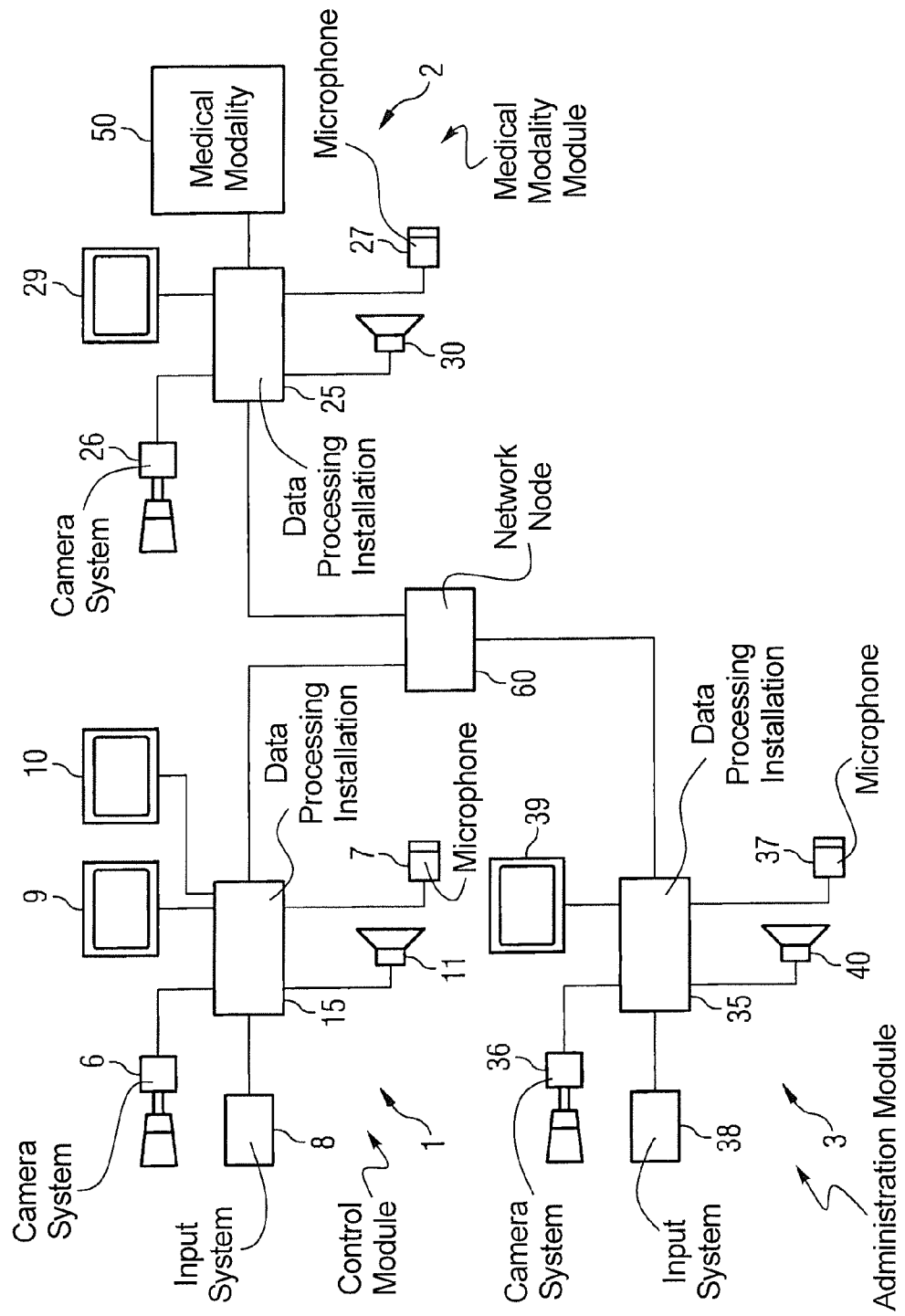

DEVICE FOR COMMUNICATION

BACKGROUND OF THE INVENTION

1. Field of the Invention

The present invention concerns a device for communication between a control module that is associated with a local operator of a medical modality, an examination module that is associated with the medical modality and an administration module that is associated with an administration facility that is remote from the medical modality, with communication units that can be connected among one another being respectively associated with each module.

2. Description of the Prior Art

Given incorrect or problematic procedures in the framework of an examination workflow at a medical modality (such as, for example, a computed tomography apparatus), the necessity regularly occurs to incorporate an administration facility (for example a remote third party) into the examination workflow in addition to the local operator.

The remote third person can be a physician, for example, who has special knowledge with regard to the examination workflow or the disease of the person to be examined. If the problem is a technical problem with the medical modality, the remote third person can be a maintenance (service) or development engineer of the manufacturer.

Conventionally, the operator (for example a physician or a nurse) informs the remote third person about the examination workflow by telephone. The remote third person is therewith disadvantageously provided with only a very limited amount of information, which can severely limit the quality of the remote diagnosis or remote administration. Moreover, conventionally only a very limited possibility, or even no possibility at all, exists to incorporate the modality or the person to be examined into the procedure. This can be necessary, however, in certain cases. Particularly in the examinations of patients who are being infused or must be specially supported, it is of the utmost importance for the control of the scan procedure that these environment parameters are taken into account, for example in order to prevent the apparatus from tearing away the infusion tube due to its movements or that patient is harmed. In the context of neurosurgery it is also of particular importance that the environmental parameters be taken into account in the control of the respective modality. The environment or context parameters are all data relevant for the examination or treatment that can be imaged by acoustic or optical or other signals and concern the context of the examination (for example questions: How is the patient supported? Is there an infusion, etc?).

Such context data are conventionally not automatically available to the maintenance engineer, who must to ask about them by telephone. This represents a significant disadvantage and risk of error.

DE 10 2004 049 402 discloses a conventional system for remote administration. Here a medical imaging system is administered by a remote operation via an operation workstation. The remote operation can be disabled in order to be able to satisfy security aspects.

One solution to circumvent the problem of telephone interrogation is taught in DE 10 2006 033 064. Here a bidirectional communication between a stationary communication unit and a mobile communication unit is supported via audio and video.

SUMMARY OF THE INVENTION

An object of the present invention is to provide a device that solves the aforementioned problems or at least reduces them.

In the following the invention is described using the solution according to a device. Mentioned advantages, features and alternative embodiments that will be described in connection with the specification of the inventive device are also applicable to the method and/or the system of the invention.

The device in accordance with the present invention for communication between a first module that is associated with a local control console of a medical modality, a second module that is associated with the medical modality (and therewith at least indirectly with a person to be examined) and a third module that is associated with an administration entity (which can be operated by a further person) remote from the medical modality includes communication units that are respectively associated with each module and that can be connected among one another in terms of data, with the signals received or sent by a respective communication unit being transferred to at least one communication unit of the other modules or to at least one other module, and the administration module can access data of the medical modality at least as needed, in particular all data that are relevant to the control of the medical modality. The communication unit of the remote administration entity has an input unit to control the medical modality and a display system. The input unit to control the medical modality via the remote administration entity can thereby be connected dependent on an indicator, and the display system identifies a presence of an operator at the medical modality with the indicator.

The inventive device allows an administration entity to directly access the data of the medical modality and to specifically interrogate either the operator and/or the examined person using the information provided by the data and/or to specifically instruct the operator and/or the examined person and/or to correspondingly control the medical modality.

A computed tomography system, a magnetic resonance tomography system, an x-ray fluoroscopy system, an angiography system or other medical apparatuses that are suitable to implement medical imaging methods are examples of "medical modality".

The term "module," as used herein means a data processing system of the type known in the prior art. The employed modules can be composed differently.

In a preferred embodiment, the second module relates to an arbitrary medical modality, the first module advantageously relates to this medical modality and the third module is an administration entity (advantageously a remote administration entity) that can be connected or disconnected as needed. The typical local console operation is then mirrored at the administration module.

A communication between three communication partners is thus typically provided. Alternatively, it is possible to form the communication only between two entities, such as between the administration module and a further (local, examination-related) module.

The signals can be acoustic, optical or other signals (for example video data etc.) that are relevant to the context of the examination to be controlled (for example the presence or absence of personnel, instructions regarding particular bearing of the patient, instructions regarding necessary medical interventions (placement of an access). The term "examination-relevant environment parameters" encompasses all the data and parameters that are relevant for the control and/or implementation of the respective examination or treatment at the modality. A selection from among such data can be considered in an alternative embodiment. This is advantageously visual information with regard to the modality and/or with regard to the patient who should be examined by the modality.

Transfer of the signals to the respective communication means can ensue by means of networks known in the prior art. Among other things this can thereby be an internet network or an internal network (known as an intranet).

Moreover, it is advantageous for each communication unit to have at least one microphone system, at least one speaker system and/or at least one camera system and at least one display system.

Via the specified systems, the possibility is afforded for the participants to communicate directly with one another in image and sound without the use of a further transmission channel being necessary (as previously, for example the use of the telephone). For example, the remote third person can immediately recognize what influence the given instructions have or whether they are correctly followed.

The visual depictions of the participating persons can be displayed, for example, in a picture-in-picture presentation or on respective individual display devices.

Moreover, the administration entity can detect whether the operator is present or not.

In an embodiment the communication unit of the remote third person includes input unit to control the medical modality.

The possibility thereby exists for the remote third instance to actively intervene in the examination workflow by taking over the control of the medical modality.

The display system of the remote third instance shows data that are displayed locally on a screen at the medical modality.

This can ensue, for example, by synchronization of at least one monitor (of the display system) of the administration entity with the monitor at the medical modality.

This affords possibility for the administration entity to record all relevant data in the same presentation form as they are displayed at the medical modality.

In a further embodiment, a device is provided for determination of the presence and/or absence of the operator at the medical modality and the administration entity is informed of the presence or absence of the operator at the medical modality and/or at the console by an indicator. The indicator can be an acoustic or optical signal.

The administration entity thereby knows in a simple manner whether the operator is present.

The administration entity is able to establish a time at which the administrative entity controls the examination workflow alone, and can possibly end the examination workflow or the control thereof in the event that a person is no longer locally on site. Sole control of the modality or the examination on the part of the administration entity can be safely precluded. This proves to be extremely important for liability reasons.

The device for determination of the presence of the operator, for example, can be a transmitter that the operator wears and a corresponding receiver that, for example, is provided in the communication unit of the modality. Monitoring the presence of the operator also can be ensued by means of the already-present camera system.

The communication units can be acoustic or optical in nature or a combination of these types. For example, an optical unit can be designed in the form of a camera system. The communication unit (for example the camera system) can be arranged only directly in the environment of the modality or in the examination room thereof, or can be cumulatively or alternatively arranged in the console room, so as to enable a visual contact with the examination room.

In a further embodiment the display system of the administration system presents information with regard to the modality or with regard to the person to be examined.

"Information of the person to be examined" encompasses such information that is normally present for the operator but not the remote third person.

Information about the feed of contrast agent, EEG charts, ECG charts and about the positioning of the person to be examined in the medical modality can in particular serve as context parameters and be displayed.

The administration entity thus can essentially monitor the entire examination workflow as well, and is not limited to only the data of the medical modality. This affords the possibility of a two-stage monitoring whereby the examination can be monitored from the console entity and from the administration entity. Moreover, the administration entity can also monitor the actions of the console entity.

According to the invention the input unit for controlling the medical modality via the administration entity can be connected dependent on the indicator that shows the presence of the operator at the medical modality.

This means that the control of the remote third person is deactivated when no operator is present at the medical modality, or the control is activated only when the indicator indicates the presence of the operator.

It can thereby be safely ensured that the administration entity is never solely responsible for the examination workflow.

The above object also is achieved by a method and in a system with features corresponding to the features described above in connection with the device.

With the inventive system it is possible for one or more entities to be connected in addition to an administration entity, or monitoring entity or an entity connected for another purpose. For example, a first physician and a second specialist can be active (perhaps in the manner of a remote consult) and can be connected in the case of a complicated neurosurgical operation using a modality.

BRIEF DESCRIPTION OF THE DRAWINGS

The single FIGURE schematically illustrates an embodiment of an inventive device operable in accordance with the inventive method.

DESCRIPTION OF THE PREFERRED EMBODIMENTS

The inventive device has a first module 1 that is associated with a control entity, a second module 2 that is associated with a medical modality (and therewith indirectly with a person to be examined) and a third module 3 that is associated with a remote administration entity with a third person. The association with the persons is here incorporated only for the purpose of better comprehensibility. The actual communication ensures between two or three communication units respectively of the console entity, the examination entity and the administration entity.

The first module 1 has a data processing installation 5 to which the following items are connected: a camera system 6, a microphone 7, an input system 8, a display system that is composed of a first monitor 9 and a second monitor 10, and a speaker system 11. The second monitor 10 is associated with a medical modality 50 and serves for the control of the medical modality 50.

The second module 2 has a data processing installation 25 to which the following items are connected: a camera system 26, a microphone 27, a display system that has a monitor 29, and a speaker system 30. The medical modality 50 that is connected with the data processing installation 25 is additionally arranged at the second module 2.

The third module 3 has a data processing installation 35 to which the following items are connected: a camera system 36, a microphone 37, an input system 38, a display system that has a monitor 39, and a speaker system 40.

The data processing installations 5, 25, 35 are connected with one another via a network node 60. This network node 60 can be a network node of an internal network or of the internet connection. It is to be understood that a number of further network nodes can be provided between the data processing systems 5, 25, 35 without deviating from the inventive concept.

The images of the camera systems of the respective modules 1, 2, 3 are presented with a format known as a picture-in-picture display.

Data about the modality or about the person to be examined (for example in which position the patient is located on bed, etc.) and an image of the monitor 10 that serves for control of the medical modality 50 can also be presented on the monitor 39 of the remote third entity. Moreover, the monitor 39 of the third entity shows whether the operator is present or not.

Via the input system 38 the administration entity can take over the control of the medical modality 50 and thereby detect whether the operator is present or not. The control of the administration entity inventively ensues via the same communication channel as the transfer of the information or context parameters relevant to the examination (or treatment) The establishment of an additional channel (for example, a telephone connection) is not necessary. Moreover, it is inventively provided that all examination-relevant information is automatically transferred to the administration module.

Although modifications and changes may be suggested by those skilled in the art, it is the intention of the inventors to embody within the patent warranted hereon all changes and modifications as reasonably and properly come within the scope of their contribution to the art.

We claim as our invention:

1. A communication device for use in a system comprising a medical modality comprising an operating console having a control module associated therewith and a medical examination unit having an examination module associated therewith, and an administration module having an administration module associated with an administration entity that is remote from said medical modality, said device comprising:

a first communication unit associated with said control module, a second communication unit associated with said examination module, and a third communication unit associated with said administration module, said first, second and third communication units being in communication with each other to allow exchange of data, represented by signals, among said control module, said examination module and said administration module;

said third communication unit at said remote administration entity comprising an input unit that allows control of the medical modality via the third control unit from the remote administration entity, and a display system;

each of said communication units comprising at least one microphone and at least one speaker allowing vocal communication among operators respectively located at said medical modality and said administration entity;

each communication unit also comprising at least one camera with a field of view at least encompassing an operator of that communication unit allowing visual communication between operations respectively located at said medical modality and said administration entity, and wherein each of said first and second communication units also comprises a display system said display system of said third communication unit displaying an indicator that indicates a presence of an operator at the medical modality and said input unit allowing control of said medical modality from said remote administration entity dependent on said indicator; and a detector that identifies a presence of said operator at said medical modality and that transmits an indicator signal to said third communication unit, other than said vocal communication and said visual communication, that causes said indicator to be displayed at said display system of said third communication unit.

2. A device as claimed in claim 1 wherein said display system of said third communication unit at said remote administration entity automatically displays all information that are displayed locally at the display system of the first communication unit at the medical modality.

3. A device as claimed in claim 1 wherein said display system of said third communication unit at said remote administration entity displays information obtained from said examination module concerning at least one of a person to be examined at said medical modality and an examination to be conducted at said medical modality.

4. A communication device as claimed in claim 1 wherein said input unit allows control of said medical modality from said remote administration entity only when said indicator indicates said presence of said operator at said medical modality.

5. A communication method for use in a system comprising a medical modality comprising an operating console having a control module associated therewith and a medical examination unit having an examination module associated therewith, and an administration module having an administration module associated with an administration entity that is remote from said medical modality, said method comprising the steps of:

associating a first communication unit with said control module, associating a second communication unit with said examination module, and associating a third communication unit with said administration module, and allowing communication among said first, second and third communication units for exchange of data, represented by signals, among said control module, said examination module and said administration module;

said third communication unit at said remote administration entity comprising an input unit and a display system, and allowing control of the medical modality via the third control unit from the input unit thereof remote administration entity;

establishing vocal and visual communication between operators respectively located at said medical modality and said administration entity by providing, at each of said communication units, at least one microphone and at least one speaker allowing vocal communication among operators respectively located at said medical modality and said administration entity, and by also providing, at each communication unit, at least one camera with a field of view at least encompassing an operator of that communication unit allowing visual communication between operations respectively located at said medical modality and said administration entity, and by providing each of said first and second communication units with a display system;

at said display system of said third communication unit, displaying an indicator that indicates a presence of an operator at the medical modality and controlling said medical modality from said remote administration entity dependent on said indicator; and at said medical modality detecting said presence of said operator at said medical modality with a detector and transmitting a signal to said administration entity from said detector, other than said vocal communication and said visual communication, that causes said indicator to be displayed at said display system of said third communication unit.

6. A communication method as claimed in claim 5 comprising allowing control of said medical modality from said remote administration entity only when said indicator indicates said presence of said operator at said medical modality.

7. A communication system comprising:

a medical modality comprising an operating console having a control module associated therewith and a medical examination unit having an examination module associated therewith;

an administration module having an administration module associated with an administration entity that is remote from said medical modality;

a first communication unit associated with said control module, a second communication unit associated with said examination module, and a third communication unit associated with said administration module, said first, second and third communication units being in communication with each other to allow exchange of data, represented by signals, among said control module, said examination module and said administration module;

said third communication unit at said remote administration entity comprising an input unit that allows control of the medical modality via the third control unit from the remote administration entity, and a display system;

each of said communication units comprising at least one microphone and at least one speaker allowing vocal communication among operators respectively located at said medical modality and said administration entity;

each communication unit also comprising at least one camera with a field of view at least encompassing an operator of that communication unit allowing visual communication between operations respectively located at said medical modality and said administration entity, and wherein each of said first and second communication units also comprises a display system;

said display system of said third communication unit displaying an indicator that indicates a presence of an operator at the medical modality and said input unit allowing control of said medical modality from said remote administration entity dependent on said indicator; and a detector that identifies a presence of said operator at said medical modality and that transmits an indicator signal to said third communication unit, other than said vocal communication and said visual communication, that causes said indicator to be displayed at said display system of said third communication unit.

8. A communication system as claimed in claim 7 wherein said input unit allows control of said medical modality from said remote administration entity only when said indicator indicates said presence of said operator at said medical modality.

\* \* \* \* \*